(12) United States Patent
Shimizu et al.

(10) Patent No.: US 11,519,010 B2
(45) Date of Patent: Dec. 6, 2022

(54) METHOD FOR PRODUCING ORGANIC SUBSTANCE

(71) Applicant: SEKISUI CHEMICAL CO., LTD., Osaka (JP)

(72) Inventors: Satoshi Shimizu, Tsukuba (JP); Kokoro Hamachi, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 17/271,483

(22) PCT Filed: Aug. 27, 2019

(86) PCT No.: PCT/JP2019/033501
§ 371 (c)(1),
(2) Date: Feb. 25, 2021

(87) PCT Pub. No.: WO2020/045422
PCT Pub. Date: Mar. 5, 2020

(65) Prior Publication Data
US 2021/0332394 A1 Oct. 28, 2021

(30) Foreign Application Priority Data
Aug. 27, 2018 (JP) .............................. JP2018-158538

(51) Int. Cl.
*C12N 1/02* (2006.01)
*C12P 7/06* (2006.01)
(Continued)

(52) U.S. Cl.
CPC .............. *C12P 7/065* (2013.01); *C12N 1/02* (2013.01); *C12N 1/20* (2013.01); *C12P 7/08* (2013.01)

(58) Field of Classification Search
None
See application file for complete search history.

(56) References Cited

U.S. PATENT DOCUMENTS 8,309,773 B2 11/2012 Jevtic et al.
2009/0215139 A1* 8/2009 Datta .................. C12P 7/08
435/162
(Continued)

FOREIGN PATENT DOCUMENTS

JP 54-16414 A 2/1979
JP 57-47471 A 3/1982
(Continued)

OTHER PUBLICATIONS

Communication, dated Mar. 11, 2021, issued by the International Bureau in International application No. PCT/JP2019/033501.
(Continued)

*Primary Examiner* — Richard C Ekstrom
(74) *Attorney, Agent, or Firm* — Sughrue Mion, PLLC (57) ABSTRACT

Provided is a method which enables efficient separation of a component such as microorganisms from an organic substance-containing liquid obtained by microbial fermentation. Disclosed is a method for producing an organic substance comprising a microbial fermentation step of obtaining an organic substance-containing liquid and a separation step of heating the organic substance-containing liquid and separating into a liquid or solid component containing microorganisms and a gaseous component containing the organic substance.

12 Claims, 2 Drawing Sheets

(51) Int. Cl.
*C12P 7/08* (2006.01)
*C12N 1/20* (2006.01)

(56) References Cited

U.S. PATENT DOCUMENTS

| | | | |
|---|---|---|---|
| 2013/0037402 A1* | 2/2013 | Pasanen | F26B 11/16 |
| | | | 202/159 |
| 2013/0149693 A1* | 6/2013 | Senaratne | C12P 7/065 |
| | | | 435/3 |
| 2016/0265008 A1* | 9/2016 | Setier | C12P 7/04 |
| 2016/0281115 A1* | 9/2016 | Hickey | C12P 7/04 |
| 2017/0260552 A1 | 9/2017 | Haas et al. | |
| 2021/0332394 A1* | 10/2021 | Shimizu | C12P 7/54 |

FOREIGN PATENT DOCUMENTS

| | | |
|---|---|---|
| JP | 05-123165 A | 5/1993 |
| JP | 08-56584 A | 3/1996 |
| JP | 2008-278825 A | 11/2008 |
| JP | 2008-545403 A | 12/2008 |
| JP | 2011-177159 A | 9/2011 |
| JP | 2014-003915 A | 1/2014 |
| JP | 2017-123791 A | 7/2017 |
| WO | WO-0068407 A1 * 11/2000 ............. C12N 1/205 |
| WO | 2011/064450 A1 6/2011 |

OTHER PUBLICATIONS

Office Action, dated Mar. 31, 2020, issued by the Japanese Patent Office in Japanese Patent Application No. 2019-555045.
International Search Report of PCT/JP2019/033501 dated Nov. 26, 2019 [PCT/ISA/210].
Extended European Search Report, dated Jun. 27, 2022, issued by the European Patent Office in European Patent Application No. 19854819.0.

* cited by examiner

METHOD FOR PRODUCING ORGANIC SUBSTANCE

CROSS REFERENCE TO RELATED APPLICATIONS

This application is a National Stage of International Application No. PCT/JP2019/033501, filed Aug. 27, 2019, claiming priority to Japanese Patent Application No. 2018-158538, filed Aug. 27, 2018.

BACKGROUND OF THE INVENTION

Field of the Invention

The present invention relates to a method for producing an organic substance and in particular, a method for producing an organic substance using an organic substance-containing liquid obtained by microbial fermentation.

Background Art

In recent years, methods for producing various organic substances from raw materials other than petroleum, for example, methods for producing bioethanol from edible raw materials such as corn by a sugar fermentation method have been of interest from the viewpoint of concerns about depletion of fossil fuel resources due to mass consumption of oils and alcohol produced from petroleum, and global environmental problems such as increase of carbon dioxide in the atmosphere. However, the sugar fermentation method using such edible raw materials has a problem of bringing about price escalation of food, for example, since the limited farmland area will be used for the production of other than food.

In order to solve such problem, investigations are made to various methods for producing various organic substances which have been conventionally produced from petroleum, using non-edible raw materials which have been disposed. For example, there is known a method for producing ethanol by microbial fermentation from iron and steel exhaust gas, syngas obtained by gasification of waste, and the like.

In a method for producing ethanol from syngas by microbial fermentation, since ethanol produced by microbial fermentation is contained in the microbial fermentation vessel, there is a need to extract ethanol therefrom. As a method for extracting such ethanol, there is known a method using a distillation device.

As a method for producing an organic substance using microorganisms, there is known a method for isolating and purifying a desired organic substance. For example, Patent Document 1 proposes a method for removing a protein remaining in a lactic fermentation liquid, in which the protein is aggregated by heat denaturation and the aggregated substance is removed by solid-liquid separation. Patent Document 2 discloses a method for purifying the organic substance using a film evaporator from an organic substance-containing liquid obtained by microbial fermentation.

PRIOR ART DOCUMENTS

Patent Document

Patent Document 1: JP2011-177159A
Patent Document 2: JP2008-545403A

SUMMARY OF THE INVENTION

Problem to be Solved

The organic substance-containing liquid obtained by the above-described microbial fermentation contains a large amount of microorganisms, dead microorganisms, proteins derived from the microorganisms, and the like, apart from the desired organic substance. Therefore, when the organic substance-containing liquid is introduced as it is into a distillation device, etc., and the organic substances is separated, the liquid or solid component such as the microorganisms increase their concentration as the organic substance is distilled off, and as a result, the viscosity of the organic substance-containing liquid in the distillation device increases to generate foaming in the distillation device, which can hinder continuous operation.

With respect to the above-described problem, it is possible to consider removing components such as the microorganisms from the organic substance-containing liquid beforehand. As a means to remove the microorganisms and the like, a membrane separation device and a centrifugal separation device have been conventionally known; however, since the filter in the membrane separation device generates clogging, it is needs to be cleaned and replaced periodically, and thus removal was difficult in a continuous manner. Further, in a centrifugation device, since the component such as the microorganisms contained in the organic substance-containing liquid is very small, there was a problem that they cannot be sufficiently separated.

It is therefore an object of the present invention to provide a method which allows removal of components such as microorganisms contained in an organic substance-containing liquid obtained by microbial fermentation, without the use of separation means such as a film separation device or a centrifugation device.

Means for Solving the Problem

The present inventors have found that the above-described object can be achieved by heating an organic substance-containing liquid obtained from microbial fermentation under a certain condition and by separating the liquid into a component such as the microorganisms as the liquid or solid component and the desired organic substance as the gaseous component. That is, the overview of the present invention is as follows.

[1] A method for producing an organic substance, comprising:
a microbial fermentation step of obtaining an organic substance-containing liquid by microbial fermentation, and
a separation step of heating the organic substance-containing liquid and separating into a liquid or solid component comprising microorganisms and a gaseous component comprising the organic substance.

[2] A method for producing an organic substance, comprising:
a microbial fermentation step of obtaining an organic substance-containing liquid comprising an organic substance having a boiling point of 115° C. or lower and an organic substance having a boiling point of over 115° C. by microbial fermentation, and
a separation step of heating the organic substance-containing liquid and separating into a liquid or solid component comprising the organic substance having a boiling point of over 115° C. and microorganisms, and a gaseous component comprising the organic substance having a boiling point of 115° C. or lower, wherein the heating temperature is from the boiling point of the organic substance having a boiling point of 115° C. or lower to 130° C.

[3] The method according to [1] or [2], further comprising a liquefaction step of liquefying the gaseous component obtained by the separation step by condensation, wherein condensation heat generated in the liquefaction step is used as a heat source.

[4] The method according to [3], further comprising a purification step of purifying an organic substance by heat distillation, wherein the condensation heat is used for a heat source of the heat distillation of the purification step.

[5] The method according to any one of [1] to [4], wherein the microbial fermentation uses a syngas comprising carbon monoxide as a raw material.

[6] The method according to [5], wherein the syngas is a waste-derived gas.

[7] The method according to any one of [1] to [6], wherein the organic substance comprises alcohol having 1 to 6 carbons.

Effect of the Invention

According to the present invention, a component such as microorganisms contained in an organic substance-containing liquid obtained by microbial fermentation can be removed without the use of separation means such as a film separation device or a centrifugation device. This makes it possible to produce an organic substance continuously.

EMBODIMENT OF THE INVENTION

Hereinafter, one example of preferred embodiments of the present invention will be described. However, the following embodiments are examples for illustrating the present invention, and the present invention is not limited in any way by the following embodiments. In the present specification, the proportion of each component in the gas is a proportion based on volume, not weight, unless otherwise specified. Thus, unless otherwise specified, percent by 100 represents percent by volume and ppm represents ppm by volume.

Figure 1:
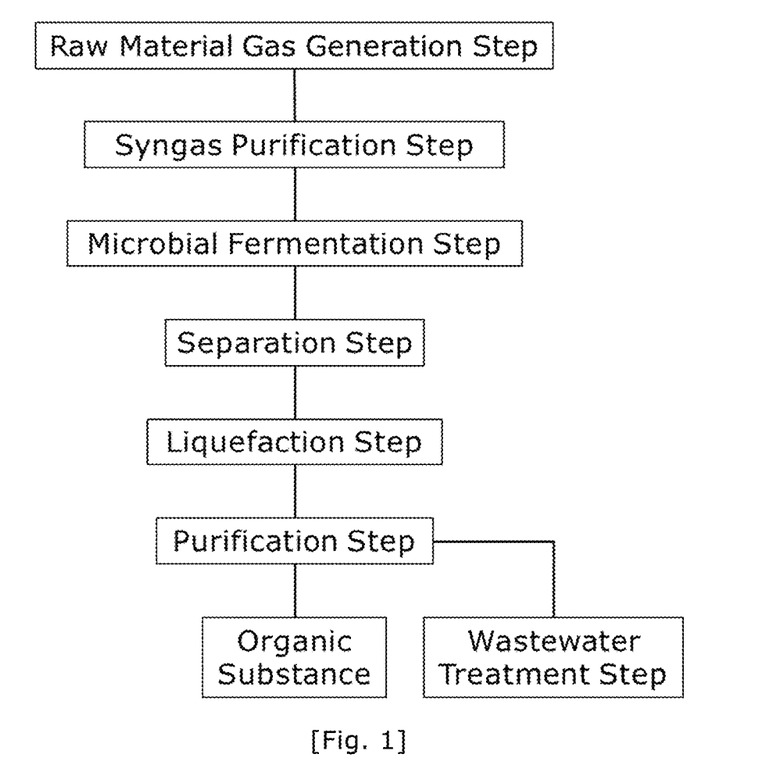
FIG. 1 is a figure of a process flow illustrating one example of the method for producing an organic substance according to the present invention.

The method for producing an organic substance according to the present invention comprises a microbial fermentation step of obtaining an organic substance-containing liquid by microbial fermentation, and a separation step of heating the organic substance-containing liquid and separating into a liquid or solid component comprising microorganisms and a gaseous component containing the organic substance. In this case, the method may further comprise a raw material gas generation step, a raw material gas purification step, a liquefaction step, a purification step, a waste water treatment step, and the like. FIG. 1 is a process flow figure indicating one example of the present invention. The process flow figure of FIG. 1 comprises a raw material gas generation step, a raw material gas purification step, a microbial fermentation step, a separation step, a liquefaction step, a purification step, and a waste water treatment step. Each step will be explained in the followings.

<Raw Material Gas Generation Step>

A raw material gas generation step is a step of generating a raw material gas by gasifying a carbon source (see FIG. 1). Note that, the raw material gas can be generated by reduction of carbon dioxide by reverse shift reaction.

There is no limitation to the raw material gas, and preferably, it contains carbon monoxide. Also, it may further contain components such as hydrogen, carbon dioxide, oxygen, nitrogen, tin, tar, nitrogen compound, sulfur compound, phosphorous compound, aromatic compound, and the like.

When the raw material gas contains carbon monoxide, the content of the carbon monoxide in the raw material gas is preferably, without particular limitation, 0.1 volume % or more, more preferably 10 volume % or more, further preferably 20 volume % or more, further preferably 20 volume % to 80 volume %, and most preferably 20 volume % to 60 volume %, with respect to the total volume of the raw material gas.

Note that a raw material gas containing carbon monoxide can generally be generated by conducting heat treatment (commonly known as gasification) in which a carbon source is subjected to combustion (incomplete combustion), i.e. by partially oxidizing the carbon source.

There is no particular limitation to the carbon source, and examples thereof include coal used in a coke oven, blast furnace (blast furnace gas), converter of a steel plant or a coal-fired power plant; waste introduced into an incinerator (especially gasification furnace) (non-industrial waste and industrial waste); biomass such as wood; and various carbon-containing materials for the purpose of recycling carbon dioxide, etc. which is sub-generated in various industries. Amongst these, the carbon source is preferably waste. In other words, the raw material gas is preferably a gas derived from waste.

Specifically, examples of the carbon source include plastic waste, garbage, municipal waste (MSW), waste tyres, biomass waste, domestic waste such as duvets and papers, waste such as building members, coal, petroleum oil, compounds derived from petroleum oil, natural gas, shale gas, and the like, and preferred amongst these is various waste, and more preferably non-segregated municipal waste from the view point of segregation costs.

Generation of the raw material gas is preferably carried out using a gasification furnace.

When a raw material gas containing carbon monoxide is generated, the gasification furnace which can be used is a furnace for combustion (incomplete combustion) of a carbon source. Specific examples include, a shaft furnace, a kiln furnace, a fluidized bed furnace, and a gasification reforming furnace. The gasification furnace is preferably a fluidized bed furnace type because a high hearth load and excellent operability can be achieved by partially combusting the waste. The waste is gasified in a fluidized bed furnace at a low temperature (about 450 to 600° C.) and in a low oxygen atmosphere to be decomposed into char containing a large amount of gas (carbon monoxide, carbon dioxide, hydrogen, methane, etc.) and carbon. In addition, since the incombustibles contained in the waste are separated from the bottom of the furnace in a hygienic and lightly oxidized state, valuable substances such as iron and aluminum in the incombustibles can be selectively recovered. Therefore, gasification of such waste enables efficient recycling of resources.

The gasification temperature in the raw material gas generating step is usually 100° C. to 1500° C. and preferably 200° C. to 1200° C.

The reaction time for gasification in the raw material gas generating step is usually 2 seconds or more and preferably 5 seconds or more.

<Raw Material Gas Purification Step>

The raw material gas as above may be supplied to the microbial fermenting vessel as a syngas as it is; however, the raw material gas may be purified so as to be suitable for the microbial fermentation.

When the raw material gas is derived from waste, the raw material gas tends to contain carbon monoxide in an amount of 0.1 volume % to 80 volume %, carbon dioxide in an amount of 0.1 volume % to 40 volume %, hydrogen in an amount of 0.1 volume % to 80 volume %, a nitrogen compound in an amount of 1 ppm or more, a sulfur compound in an amount of 1 ppm or more, a phosphorus compound in an amount of 0.1 ppm or more and/or an aromatic compound in an amount of 10 ppm or more. It may also contain substances such as other environmental contaminants, soot and dust particles, and impurities. Therefore, when the syngas is supplied to the microbial fermenting vessel, it is preferable to reduce or remove substances that are unfavorable for stable culturing of microorganisms and compounds in an undesired amount, and the like from the raw material gas so that the content of each component contained in the raw material gas is in a range suitable for stable culturing of microorganisms.

That is, the raw material gas purification step is a step of removing or reducing a specific substance such as various contaminants, soot and dust particles, impurities, and undesired amounts of compounds from the raw material gas (see FIG. 1). In the pretreatment step, syngas may be obtained from the raw material gas. The pretreatment step can be carried out using one or two or more of, for example, a gas chiller (a water separator), a low temperature (cryogenic) separation device, a cyclone, a particulate (soot) separator such as a bag filter, a scrubber (a water-soluble impurity separator), a desulfurizer (a sulfide separator), a membrane separator, a deoxygenator, a pressure swing adsorption separator (PSA), a temperature swing adsorption separator (TSA), a pressure temperature swing adsorption separator (PTSA), a separator using activated carbon, a separator using a copper or a palladium catalyst.

The raw material gas (hereinafter, the gas obtained by purifying the raw material gas may be referred to as "syngas") used in the method for producing an organic substance of the present invention preferably contains carbon monoxide. It may further contain hydrogen, carbon dioxide, and nitrogen.

The syngas used in the present invention may be a gas obtained by carrying out the steps of gasifying a carbon source to generate a raw material gas (a raw material gas generating step), and then adjusting the concentration of each component of carbon monoxide, carbon dioxide, hydrogen, and nitrogen and reducing or removing the above-mentioned substances and compounds from the raw material gas.

The concentration of carbon monoxide in the syngas is usually 20 volume % to 80 volume %, preferably 25 volume % to 50 volume %, and more preferably 35 volume % to 45 volume %, with respect to the total concentration of the carbon monoxide, carbon dioxide, hydrogen, and nitrogen in the syngas.

The concentration of hydrogen in the syngas is usually 10 volume % to 80 volume %, preferably 30 volume % to 55 volume %, and more preferably 40 volume % to 50 volume % with respect to the total concentration of carbon monoxide, carbon dioxide, hydrogen, and nitrogen in the syngas.

The concentration of carbon dioxide in the syngas is usually 0.1 volume % to 40 volume %, preferably 0.3 volume % to 30 volume %, more preferably 0.5 volume % to 10 volume %, and particularly preferably 1 volume % to 6 volume %, with respect to the total concentration of carbon monoxide, carbon dioxide, hydrogen, and nitrogen in the syngas.

The concentration of nitrogen in the syngas is usually 40 volume % or less, preferably 1 volume % to 20 volume %, and more preferably 5 volume % to 15 volume %, with respect to the total concentration of carbon monoxide, carbon dioxide, hydrogen, and nitrogen in the syngas.

The concentration of carbon monoxide, carbon dioxide, hydrogen, and nitrogen can be set to a predetermined range by changing the C—H—N element composition of the carbon source in the raw material gas generating step or by changing the combustion conditions such as the combustion temperature and the oxygen concentration of the supply gas during combustion, if necessary. For example, in the case where the concentration of carbon monoxide or hydrogen is to be changed, a carbon source having a high C—H ratio such as waste plastic may be used, and in the case where the concentration of nitrogen is to be lowered, gas having a high oxygen concentration may be supplied in the raw material gas generating step.

The syngas used in the present invention may, without particular limitation, contain a sulfur compound, a phosphorus compound, a nitrogen compound and the like in addition to the above components. The content of each of these compounds is preferably 0.05 ppm or more, more preferably 0.1 ppm or more, further preferably 0.5 ppm or more. The content of each compound is preferably 2000 ppm or less, more preferably 1000 ppm or less, further preferably 80 ppm or less, further more preferably 60 ppm or less, and particularly preferably 40 ppm or less. When the content of the sulfur compound, the phosphorus compound, the nitrogen compound, etc. is no less than the lower limit, there is an advantage that the microorganisms can be suitably cultured, and when the content is no more than the upper limit, there is an advantage that the culture medium is not contaminated by various nutrition sources which the microorganisms have not consumed.

Examples of the sulfur compound include sulfur dioxide, $CS_2$, COS, and $H_2S$, and preferred amongst them are $H_2S$ and sulfur dioxide as they are easily consumed as a nutrition source for the microorganisms. Therefore, it is more preferable that the syngas contains the sum of $H_2S$ and sulfur dioxide within the above ranges.

As the phosphorus compound, phosphoric acid is preferred as it is easily consumed as a nutrition source for the microorganisms. Therefore, it is more preferable that the syngas contains phosphoric acid within the above ranges.

Examples of the nitrogen compound include nitrogen monoxide, nitrogen dioxide, acrylonitrile, acetonitrile, HCN, and the like, and HCN is preferable in that it is easily consumed as a nutrient source for the microorganisms. Therefore, it is more preferable that the syngas contains HCN in the above range.

The syngas may contain an aromatic compound in the amount of preferably 0.01 ppm or more, more preferably 0.03 ppm or more, further preferably 0.05 ppm or more, and particularly preferably 0.1 ppm or more. The content of the aromatic compound is also preferably 90 ppm or less, more preferably 70 ppm or less, further preferably 50 ppm or less, and particularly preferably 30 ppm or less. By containing the aromatic compound in an amount no less than the lower limit, the microorganisms tend to be cultured suitably. On the other hand, when the aromatic compound is contained in an amount no more than the upper limit, the culture medium tends to be less contaminated by various nutrition sources which the microorganisms have not consumed.

Note that, as mentioned above, the syngas is a purified gas of the raw material gas, and preferably, the raw material gas is a gas derived from waste. Therefore, the syngas is preferably a gas derived from waste.

<Microbial Fermentation Step>

A microbial fermentation step is a step of obtaining an organic substance-containing liquid by microbial fermentation (see FIG. 1). In this case, normally a raw material gas obtainable from the raw material gas generation step or from a raw material gas (syngas) obtainable from the raw material gas purification step may be used in the microbial fermentation. Preferred amongst these is the use of the syngas in view of carrying out microbial fermentation in a suitable manner. Use may also be made to a syngas obtained by adding another predetermined gas to the raw material gas obtainable from the raw material gas generation step or the gas (syngas) obtainable from the raw material gas purification step. Examples of the other predetermined gas include at least one compound selected from the group consisting of sulfuric compounds such as sulfur dioxide, phosphorus compounds, and nitrogen compounds. In one embodiment, the microbial fermentation preferably uses the raw material gas containing carbon monoxide or the syngas containing carbon monoxide as a raw material, and more preferably, the syngas containing carbon monoxide as a raw material. In this case, the raw material gas or the syngas is preferably a gas derived from waste. Herein under, the raw material gas or the syngas used in the microbial fermentation may be collectively referred to as "syngas, etc.".

Microbial fermentation is generally conducted in a microbial fermenting vessel. The microbial fermenting vessel used is preferably a continuous fermenter. In general, the microbial fermenting vessel may be of any shape, including a stirred type, an airlift type, a bubble column type, a loop type, an open-bond type, and a photobio type. Suitably used amongst these are known loop reactors having a main vessel part and a reflux part. When the loop reactors are used, a circulation step is preferably included, in which a liquid medium is circulated in between the main vessel part and the reflux part.

Although the syngas and the microbial culture solution may be continuously fed to the microbial fermenting vessel, the syngas and the microbial culture solution need not be fed simultaneously, and the syngas may be fed to the microbial fermenting vessel to which the microbial culture solution has been previously fed. It is known that some anaerobic microorganisms produce organic substances which are valuables such as ethanol, from a substrate gas such as a syngas by the fermenting action, and these gas-utilizing microorganisms are cultured in a liquid medium. For example, the liquid medium and the gas-utilizing bacteria may be fed and stored, and while the liquid medium is stirred in this state, the syngas may be fed into the microbial fermenting vessel. Accordingly, the gas-utilizing bacteria can be cultured in a liquid medium and by the fermenting action, an organic substance can be produced from the syngas.

As the temperature of the medium (culture temperature) in the microbial fermenting vessel, any temperature may be employed, and preferably can be about 30 to 45° C., more preferably about 33 to 42° C., and further preferably about 36.5 to 37.5° C.

The preferred culture time is 12 hours or longer with continuous culture, more preferably 7 days or longer, particularly preferably 30 days or longer, and most preferably 60 days or longer. Note that, the upper limit of the culture time is not determined; however, in view of periodic maintenance of the facility, the culture time is preferably 720 days or shorter and more preferably 365 days or shorter. Note that, the culture time is referred to as the time from adding the seed bacteria to the culturing vessel to the time when the entire amount of the culture solution in the culturing vessel is discharged.

Figure 2:
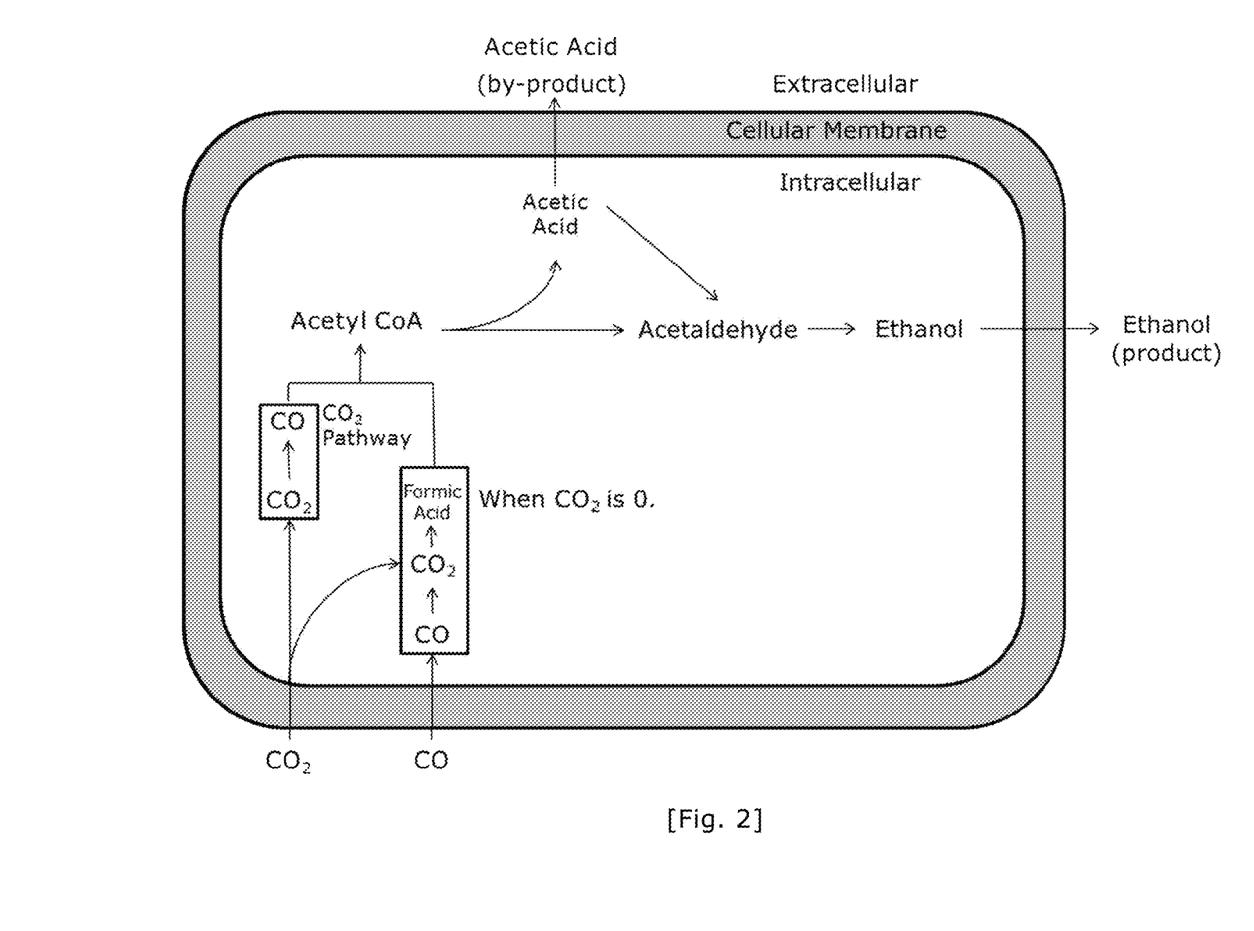
FIG. 2 is a figure illustrating a pathway to generate ethanol by fermentation effect of microorganisms.

The microorganisms (species) contained in the microbial culture solution are preferably those that can produce a desired organic substance by microbial fermentation of syngas using carbon monoxide as a main raw material (see FIG. 2). For example, the microorganisms (species) are preferably microorganisms which generate an organic substance from the syngas by the fermenting action of gas-utilizing bacteria, and particularly preferably microorganisms having a metabolic pathway of acetyl CoA. Among the gas-utilizing bacteria, the genus *Clostridium* is more preferred, and *Clostridium autoethanogenum* is particularly preferred, without particular limitation. The following is a further example.

Gas-utilizing bacteria include both eubacteria and archaebacteria. Examples of the eubacteria include *Clostridium, Moorella, Acetobacterium, Carboxydocella, Rhodopseudomonas, Eubacterium, Butyribacterium, Oligotropha, Bradyrhizobium*, and aerobic hydrogen-oxidizing bacteria, Ralsotonia bacteria, and the like.

On the other hand, examples of the archaebacteria include bacteria from the genus of *Methanobacterium, Methanobrevibacter, Methanocalculus, Methanococcus, Methanosarcina, Methanosphaera, Methanothermobacter, Methanothrix, Methanoculleus, Methanofollis, Methanogenium, Methanospirillium, Methanosaeta, Thermococcus, Thermofilum, Arcaheoglobus*, and the like. Amongst these, preferred as the archaebacterial are *Methanosarcina, Methanococcus, Methanothermobacter, Methanothrix, Thermococcus*, Thermofilum, and *Archaeoglobus*.

Further, preferred as the archaebacteria are bacteria from the genus of *Methanosarcina, Methanothermobactor*, or *Methanococcus*, and particularly preferred are *Methanosarcina* or *Methanococcus*, due to excellent carbon monoxide and carbon dioxide utilizing properties. Specific examples of the bacteria from the genus of *Methanosarcina* include *Methanosarcina barkeri, Methanosarcina mazei, Methanosarcina acetivorans*, and the like.

Among the above gas-utilizing bacteria, bacteria having a high ability to produce organic substances of interest can be selected and used. For example, the gas-utilizing bacteria having a high ethanol-producing ability include *Clostridium autoethanogenurn, Clostridium I jungdahlii, Clostridium aceticum, Clostridium carboxidivorans, Moorella thermoacetica, Acetobacterium woodii*. Among these, *Clostridium autoethanogenum* is particularly preferable.

The medium used for culturing the above-described microorganisms (species) is not particularly limited, as long as it has an appropriate composition corresponding to the microorganisms, and is a liquid containing water as a main component and a nutrient (for example, vitamin, phosphoric acid, etc.) dissolved or dispersed in the water. The composition of such medium is prepared so that the gas-utilizing bacteria may grow well. For example, the medium in which the genus *Clostridium* is used as the microorganism can be prepared by using the specification of US2017/260552, paragraphs [0097] to [0099], etc. as a reference.

The organic substance-containing liquid obtained from the microbial fermentation step includes the organic substance and other components.

Examples of the organic substance include, alcohols having 1 to 6 carbons, diols having 1 to 6 carbons, carboxylic acids having 1 to 6 carbons, hydroxycarboxylic acids having 1 to 6 carbons, ketones having 3 to 6 carbons, alkenes having 2 to 6 carbons, and alkadienes having 2 to 6 carbons.

Examples of the alcohols having 1 to 6 carbons include methanol, ethanol, propanol, isopropyl alcohol, and the like.

Examples of the diols having 1 to 6 carbons include 2,3-butanediol, and the like.

Examples of the carboxylic acids having 1 to 6 carbons include acetic acid, and the like.

Examples of the hydroxycarboxylic acids having 1 to 6 carbons include lactic acid, and the like.

Examples of the ketones having 3 to 6 carbons include acetone, and the like.

Examples of the alkenes having 2 to 6 carbons include isoprene, and the like.

Examples of the alkadienes having 2 to 6 carbons include butadiene, and the like.

Amongst these, preferably included as the organic substance are the alcohols having 1 to 6 carbons and the diols having 1 to 6 carbons, more preferably ethanol, propanol, isopropyl alcohol, and 2,3-butanediol, and further preferably ethanol. Note that, one of the organic substances as above may be contained alone, or 2 or more in combination.

In one embodiment, the organic substance is preferably one that has a boiling point of 115° C. or lower, and preferably ethanol, propanol, isopropyl alcohol, acetone, isoprene, and butadiene, more preferably ethanol, propanol, isopropyl alcohol, and acetone, further preferably ethanol and acetone, and particularly preferably ethanol.

Examples of the other components include, without particular limitation, microorganisms and dead microorganisms, proteins derived from the microorganisms, components derived from medium, water, and the like.

Normally, the organic substance-containing liquid is obtained as a suspension. In this case, the protein concentration in the suspension varies depending on the kind of microorganisms, and normally is 30 to 1000 mg/L. Note that, the protein concentration in the organic substance-containing liquid can be measured by Kjeldahl method.

Note that, the organic substance-containing liquid can be subjected to solid liquid separation such as a pressing machine, a centrifugation machine, and a filter and a part of the desired organic substance can be separated beforehand. This allows separation into a purified liquid containing the desired organic substance and the organic substance-containing liquid containing microorganisms, etc. As a result, the total amount of the organic substance-containing liquid to be separated from the separation step to be described later is reduced, and the separation step can be conducted efficiently. In this case, the purified liquid containing the desired organic substance can be directly introduced to the purification step to be described later.

<Separation Step>

A separation step is a step of heating the organic substance-containing liquid and separating into a liquid or solid component comprising the microorganisms and a gaseous component comprising the organic substance (see FIG. 1).

In conventional methods, when the organic substance-containing liquid obtained from the microbial fermentation step is directly subjected to purification of the organic substance by the purification step such as distillation as above, there was a problem that foaming is generated induced by the microorganisms and proteins derived from the microorganisms, interrupting the continuous operation.

There was also a problem that even when the microorganisms and proteins derived from the microorganisms in the organic substance-containing liquid were attempted to be removed by a film separation device or a centrifugation device, periodic washing and replacement of the filter were required in the case in which the film separation device was used due to clogging, and separation was insufficient in the case in which the centrifugation device was used.

To such problem, the present invention utilizes the change in state by heating. That is, by heating the organic substance-containing liquid, the organic substance is turned into gas and the microorganisms and the proteins derived from the microorganisms are turned into liquid or solid, which makes it possible to separate only the desired organic substance. The separation step by heating requires no operation like washing and replacing the filter unlike the case using the conventional film separation device, and sufficient separation can be conducted unlike the case using the centrifugation device. Further, removing the microorganisms and the proteins derived from the microorganisms in the organic substance-containing liquid beforehand prevents from happening, for example, an event like interrupting continuous operation due to foaming in the subsequent distillation device as it has been conventionally. This allows manufacturing of the organic substance continuously.

Examples of the liquid or solid component are a component that may turn into a liquid or solid state after heating the organic substance-containing liquid. Specific examples include, microorganisms, residues of the microorganisms, proteins derived from the microorganisms, components derived from the medium, and water.

The gaseous component comprises the organic substance. The gaseous component may further comprise substances that turn into a gas state after heating the organic substance-containing liquid. Particular examples include water, in addition to organic substances.

The heating temperature of the organic substance-containing liquid varies depending on the kind of organic substances, and preferably is from 30 to 500° C., more preferably is from 50 to 200° C., further preferably is from 80 to 180° C., and particularly preferably is from 100 to 150° C.

The pressure at the time of heating is preferably 0.00001 to 1 MPa, more preferably 0.01 to 0.2 MPa, and further preferably 0.05 to 0.15 MPa. When the organic substance-containing liquid is heated by vapor, the pressure at the time of heating can be controlled in view of adjusting the heating temperature.

The heating of the organic substance-containing liquid as above is preferably done at 50 to 200° C., more preferably at 80 to 180° C., further preferably at 90 to 150° C., and particularly preferably at 95 to 120° C., in view of economic efficiency, under normal pressure (101.3 kPa).

The heating time in the separation step varies depending on the heating condition, and there is no particular limitation as long as the time is sufficient for obtaining the gaseous component. The heating time in the separation step is normally 5 seconds to 2 hours, preferably 5 seconds to 1 hour, and more preferably 5 seconds to 30 minutes, in view of efficiency and economic efficiency.

When a plurality of organic substances is generated by microbial fermentation, it is preferable to separate only the desired organic substance.

In this case, the desired organic substance is preferably one having a boiling point of 115° C. or lower, preferably ethanol, propanol, isopropyl alcohol, acetone, isoprene, and butadiene, more preferably ethanol, propanol, isopropyl alcohol, and acetone, further preferably ethanol and acetone, and particularly preferably ethanol.

The undesired organic substance is preferably one having a boiling point of over 115° C., preferably 2,3-butanediol, acetic acid, and lactic acid, and more preferably 2,3-butanediol and acetic acid.

In this case, the liquid or solid component comprises the undesired organic substance, microorganisms, residues of the microorganisms, proteins derived from the microorganisms, components derived from the medium, and water. In this case, the desired organic substance can also be contained.

The gaseous component comprises the desired organic substance. The gaseous component may additionally contain water. Optionally, the gaseous component can contain the undesired organic substance.

In one embodiment, the desired organic substance is one having a boiling point of 115° C. or lower, and the undesired organic substance is one having a boiling point of over 115° C. In this case, the separation step is a step of heating the organic substance-containing liquid comprising the organic substances having a boiling point of 115° C. or lower and a boiling point of over 115° C. and separating into a liquid or solid component comprising the organic substance having a boiling point of over 115° C. and a gaseous component comprising the organic substance having a boiling point of 115° C. or lower.

In this case, the heating temperature of the organic substance-containing liquid is preferably from the boiling point of the organic substance having a boiling point of 115° C. to 130° C., more preferably from 10° C. higher than the boiling point of the organic substance having a boiling point of 115° C. or lower to 120° C., further preferably from 20° C. higher than the boiling point of the organic substance having a boiling point of 115° C. or lower to 110° C., and particularly preferably from 20° C. higher than the boiling point of the organic substance having a boiling point of 115° C. or lower to 103° C. The heating temperature is preferred to be within the above-described ranges since the desired organic substance having a boiling point of 115° C. or lower can be turned into a gaseous component and the undesired organic substance having a boiling point of over 115° C. can be turned into a solid or liquid component.

That is, according to one embodiment of the present invention, there is provided a method for producing an organic substance, comprising:

a microbial fermentation step of obtaining the organic substance-containing liquid comprising an organic substance having a boiling point of 115° C. or lower and an organic substance having a boiling point of over 115° C. by microbial fermentation, and a separation step of heating the organic substance-containing liquid and separating into a liquid or solid component comprising the organic substance having a boiling point of over 115° C. and microorganisms and a gaseous component comprising the organic substance having a boiling point of 115° C. or lower, wherein the heating is done under the temperature from the boiling point of the organic substance having a boiling point of 115° C. or lower to 130° C.

In one embodiment of the present invention, the desired organic material comprises ethanol and the undesired organic material comprises at least one of 2,3-butanediol and acetic acid. In this case, the separation step is a step of heating the organic substance-containing liquid comprising ethanol and at least one of 2,3-butanediol and acetic acid and separating the liquid or solid component containing microorganisms and at least one of 2,3-butanediol and acetic acid into a gaseous component comprising ethanol.

In this case, the heating temperature of the organic substance-containing liquid is preferably 78° C. to 130° C., more preferably 88° C. to 120° C., still more preferably 98° C. to 110° C., and particularly preferably 98° C. to 103° C.

That is, according to one embodiment of the present invention, there is provided a method for manufacturing an organic substance, comprising a microbial fermentation step of obtaining an organic substance-containing liquid comprising ethanol and at least one of 2,3-butanediol and acetic acid by microbial fermentation, and a separation step of heating the organic substance-containing liquid and separating into a liquid or solid component comprising at least one of 2,3-butanediol and acetic acid and microorganisms and a gaseous component comprising ethanol, wherein the heating is carried out at 78 to 130° C.

It is more preferable that the manufacturing method comprises a microbial fermentation step of obtaining an organic substance-containing liquid comprising ethanol and 2,3-butanediol and acetic acid by microbial fermentation, and a separation step of heating the organic substance-containing liquid and separating into a liquid or solid component comprising 2,3-butanediol and acetic acid and microorganisms and a gaseous component containing ethanol.

The device used in the above-described separation step is not particularly limited, as long as it can efficiently separate the organic substance-containing liquid into a liquid or a solid component (microorganisms, dead microorganisms, proteins derived from the microorganisms, etc.) and a gaseous component (the organic substance) by heat energy. Examples of specific devices include drying devices such as a rotary dryer, a fluidized bed dryer, a vacuum type dryer, and a conduction heating type dryer. Among these, from the viewpoint of efficiency in separating the liquid or solid component and the gaseous component from the organic substance-containing liquid particularly having a low solid component concentration, it is preferable to use a conduction heating type dryer. Examples of the conduction heating type dryer include a drum type dryer and a disk type dryer.

<Liquefaction Step>

The liquefaction step is a step of liquefying the gaseous component containing the organic substance obtained in the separation step above by condensation (see FIG. 1). The device used in the liquefaction step is preferably, without particular limitation, a heat exchanger, particularly a condenser. Examples of the condenser include a water-cooled condenser, an air-cooled condenser, and an evaporation condenser. Among them, the water-cooled type is preferable. The condenser may be of a single stage or multiple stages.

Although it is deemed preferable that the liquefied product obtained by the liquefaction step is free of the components comprised in the organic substance-containing liquid such as microorganisms, dead microorganisms, proteins derived from the microorganisms, and the like, the present invention does not exclude the presence of proteins in the liquefied product. Even when proteins are contained in the liquefied product, the concentration thereof is preferably 40 mg/L or less, more preferably 20 mg/L or less, and further preferably 15 mg/L or less.

Note that, condensation heat of the gaseous component is generated in the liquefaction step. The condensation heat generated in this liquefaction step can be used as a heat source as described later.

<Purification Step>

A purification step is a step of purifying an organic substance (see FIG. 1). In this case, said purification means that the organic substance-containing liquid is separated into a distillate in which the concentration of the target organic substance is increased and a bottom product in which the concentration of the target organic substance is decreased. The organic substance to be purified may be a purified liquid comprising an organic substance separated after the microbial fermentation step, or may be a liquefied product obtained by condensing a gaseous component obtained after the separation step, or may be a mixture thereof.

Examples of the device used in the purification step include a distillation device, a treatment device including a pervaporation membrane, a treatment device including a zeolite dehydration membrane, a treatment device for removing a low boiling point substance having a boiling point lower than that of the organic substance, a treatment device for removing a high boiling point substance having a boiling point higher than that of the organic substance, and a treatment device including an ion exchange membrane. These devices may be used alone or two or more in combination. Suitable use made for the unit operation is heat distillation or membrane separation.

Among these, the purification step preferably includes heat distillation. That is, in one embodiment, the method preferably comprises a purification step of purifying the organic substance by heat distillation.

In the heat distillation, a desired organic substance can be obtained as a distillate with high purity using a distillation device.

The temperature in the distillation device at the time of distillation of the organic substance (particularly ethanol) is not particularly limited, and is preferably 110° C. or less, more preferably 100° C. or less and further preferably about 70 to 95° C. Setting the temperature in the distillation device within the above range will ensure necessary separation of the organic substance from the other components, i.e., distillation of the organic substance.

The pressure in the distillation device during distillation of the organic substance may be a normal pressure; however, preferred pressure is less than normal pressure and more preferred is about 60 to 95 kPa (absolute pressure). Setting the pressure in the distillation device within the above range allows improvement of the separation efficiency of the organic substance, which can lead to improvement in the yield of the organic substance. Although depending on the kind of the desired organic substance, the yield when, for example the organic substance is ethanol, (concentration of ethanol contained in the distillate after distillation) is preferably 90% by weight or more and more preferably 95% by weight or more.

In the membrane separation, a known separation membrane can be used appropriately, for example, a zeolite membrane can be used appropriately.

The concentration of the organic substance comprised in the distillate separated in the purification step is preferably 20 to 99.99% by mass and more preferably 60 to 99.9% by mass.

On the other hand, the concentration of the organic substance comprised in the bottom product is preferably 0.001 to 10% by mass and more preferably 0.01 to 5% by mass.

The bottom product separated in the purification step is substantially free of a nitrogen compound. In the present invention, "substantially free" does not mean that the concentration of the nitrogen compound is 0 ppm, but means that the concentration of the nitrogen compound in the bottom product obtained in the purification step is in a level that requires no waste water treatment step. In the separation step, the organic substance-containing liquid is separated into a liquid or solid component comprising the microorganisms and a gaseous component comprising the organic substance as described above, and the desired organic substance is not purified from the organic substance-containing liquid obtained in the microbial fermentation step. In this case, since the nitrogen compound remains in the liquid or solid component side comprising the microorganisms, the gaseous component comprising the organic substance contains almost no nitrogen compound. Therefore, it is considered that the nitrogen compound is substantially not contained in the bottom product obtained when the organic substance is purified from the liquefied product obtained by liquefying the gaseous component. Even when the bottom product contains a nitrogen compound, the concentration of the nitrogen compound is 0.1 to 200 ppm, preferably 0.1 to 100 ppm, and more preferably 0.1 to 50 ppm.

For the same reason as described above, the bottom product separated in the purification step is substantially free of a phosphorus compound. Note that, "substantially free" does not mean that the concentration of the phosphorus compound is 0 ppm, but means that the concentration of the phosphorus compound in the bottom product obtained in the purification step is in a level that requires no waste water treatment step. Even when the bottom product contains a phosphorus compound, the concentration of the phosphorus compound is 0.1 to 100 ppm, preferably 0.1 to 50 ppm, more preferably 0.1 to 25 ppm. As described above, according to the method of the present invention, it is considered that the bottom product discharged in the purification process of the organic substance does not substantially contain the nitrogen compound or the phosphorus compound, and hardly contains other organic substances, and thus the waste water treatment step conventionally required can be simplified.

<Wastewater Treatment Step>

The bottom product separated in the purification step may be subjected to a waste water treatment step (see FIG. 1). In the waste water treatment step, organic substances such as the nitrogen compound and the phosphorus compound can be further removed from the bottom product. In this step, the organic substance may be removed by subjecting the bottom product to anaerobic treatment or aerobic treatment. The removed organic substance may be used as a fuel (heat source) in the purification process.

The treatment temperature in the waste water treatment step is usually 0 to 90° C., preferably 20 to 40° C., and more preferably 30 to 40° C.

Since the liquid or solid component comprising microorganisms and the like are removed from the bottom product obtained through the separation step, the load of waste water treatment, etc. is reduced compared with the bottom product obtained by directly supplying the purification step from the microbial fermentation step.

In the waste water treatment step, the concentration of the nitrogen compound in the treated liquid obtained by treating the bottom product is preferably 0.1 to 30 ppm, more preferably 0.1 to 20 ppm, and further preferably 0.1 to 10 ppm, and particularly preferably, no nitrogen compound is contained. The concentration of the phosphorus compound in the treatment liquid is preferably 0.1 to 10 ppm, more preferably 0.1 to 5 ppm, and further preferably 0.1 to 1 ppm, and particularly preferably, no phosphorus compound is contained in the bottom product.

<Use of Condensation Heat Generated in Liquefaction Step>

As described above, condensation heat generated in the liquefaction step can be used as a heat source. By utilizing the condensation heat, the organic substance can be produced efficiently and economically.

The region in which the condensation heat is used may be, without particular limitation, any of a raw material gas generation step, a raw material gas purification step, a microbial fermentation step, a separation step, a purification step, and a waste water treatment step.

When the condensation heat is used as a heat source in the raw material gas generation step, the condensation heat can be used as a heat source for the gasification of the carbon source.

When the condensation heat is used as a heat source in the raw material gas purification step, the condensation heat can be used as, for example, a heat source for a temperature swing adsorption separator (TSA) or a pressure temperature swing adsorption separator (PTSA).

When the condensation heat is used as a heat source in the microbial fermentation step, the condensation heat can be used as, for example, a heat source for maintaining the culture temperature.

When the condensation heat is used as a heat source in the separation step, the condensation heat can be used as, for example, a heat source for heating the organic substance-containing liquid.

When the condensation heat is used as a heat source in the purification step, the condensation heat can be used, for example, as a heat source for heat distillation.

When the condensation heat is used as a heat source in the waste water treatment step, the condensation heat can be used as, for example, a heat source for the waste water treatment temperature.

Among these, it is preferable to use the condensation heat as a heat source for heat distillation in the purification step. That is, in one embodiment of the present invention, the method for producing an organic substance comprises a liquefaction step of condensing and liquefying a gaseous component obtained in the separation step, and a purification step of purifying the organic substance from the liquefied product obtained in the liquefaction step by heat distillation, and it is preferable that the condensation heat generated in the liquefaction step is used as a heat source for heat distillation in the purification step.

The organic substance obtained by the liquefaction step may be subjected to a purification step of purifying the organic substance by heat distillation as described above. In this case, the condensation heat is generated near the point where heat distillation is performed. Therefore, use of the condensation heat as a heat source as is for heat distillation existing nearby allows efficient use of the condensation heat. Further, since the portion generating the condensation heat and the heat distillation portion are close to each other, the piping for transporting the heat source can be shortened, allowing a cost reduction. Note that, the piping generally has a heat retaining function and durability, which may affect the cost of the device.

By using the condensation heat generated in the liquefaction step as a heat source for the heat distillation instead of using the gaseous component obtained in the separation step as it is as a heat source for the heat distillation, the organic substance and the heat source can be separated and as a result, the heat source can be utilized efficiently. For example, in the case of heat distillation, the organic substance is usually introduced from the bottom of the distillation column. Therefore, it is not deemed efficient when the gaseous component obtained in the separation step is introduced from the bottom of the column, in terms of heating. On the other hand, by separating the organic substance and the heat source (for example, steam) by the liquefaction process, the organic substance can be introduced from the bottom of the column, and the heat source (for example, steam) can, for example, be introduced into the lower part, the middle part, and the upper part of the side wall of the distillation column, so that efficient heating can be performed.

<Organic Substance and Use Thereof>

The use of the organic substance obtained by the production method of the present invention is not particularly limited. The produced organic substance can be used as a raw material for, for example, plastics, resins, and the like, and can also be used as various solvents, fungicides, or fuels. The high-concentration ethanol can be used as fuel ethanol mixed with gasoline, etc., and can also be used as an additive for cosmetics, beverages, chemical substances, raw materials of fuels (jet fuel), food, etc., having extremely high versatility.

EXAMPLES

The present invention will be described in more details with reference to Examples; however, the present invention is not limited to the following Examples to the extent the scope of the invention is not exceeded.

Example 1

A continuous fermenter (fermenting vessel) provided with a main reactor, a syngas supply hole, a medium supply hole, and a discharge hole was filled with a seed bacteria of *Clostridium autoethanogenum* (microorganism) and a liquid culture medium (containing an appropriate amount of a phosphorus compound, a nitrogen compound, various minerals, and the like) for culturing the bacteria.

Next, a syngas composed of 30 volume % of carbon monoxide, 10 volume % of carbon dioxide, 35 volume % of hydrogen and 25 volume % of nitrogen was prepared, fed into the continuous fermenter, and culture (microbial fermentation) was carried out at 37° C.

After the culture, the organic substance-containing liquid discharged from the microbial fermenting vessel was collected. The obtained organic substance-containing liquid was a suspension containing ethanol, 2,3-butanediol (2,3-BDO), acetic acid, microorganisms, dead microorganisms, water, and the like, and the concentration of the proteins in the organic substance-containing liquid was 170 mg/L. Note that, the concentration of the proteins was measured in accordance with Kjeldahl method.

A hollow disc (disc) provided in a conduction heating type drying device (CD dryer, SCD-500, manufactured by Nishimura Works Co., Ltd.) was heated at 120 to 125° C. under normal pressure (0.1 MPa) (disc surface temperature: 100° C.), and the organic substance-containing liquid obtained by culturing was brought into contact with the heated disc to separate a liquid or solid component and a gaseous component. The separated gaseous component was condensed by a condenser and liquefied to obtain a liquefied product. The protein concentration in the resulting liquefied product was determined to be 13 mg/L.

In the case when ethanol was deemed as the desired organic substance, and 2,3-BDO and acetic acid as the undesired organic substance, each of the contents of ethanol (boiling point: 78° C.), 2,3-BDO (boiling point: 177° C.), acetic acid (118° C.) and water in the first organic substance-containing liquid was measured, and the recovery rates were calculated. As a result, the recovery rate of ethanol was 93 volume %, the recovery rate of 2,3-BDO was 56 volume %, the recovery rate of acetic acid was 58 volume %, and the recovery rate of water was 100 volume %. The results obtained are shown in Table 1 below.

Note that, assuming the distillation process is to be carried out in the distillation column, a foaming test was conducted by bubbling while the obtained liquefied product was heated, and almost no foaming was confirmed.

Example 2

A liquefied product was obtained in the same manner as in Example 1, except that the pressure at the time of heating in the conduction heating type drying device was set to 0.15 MPa and the surface temperature of the hollow disc (disc) was changed to 115° C.

The recovery rates of ethanol, 2,3-BDO, acetic acid, and water were determined in the same manner as in Example 1 and were 95 volume %, 78 volume %, 74 volume %, and 100 volume %, respectively. The results obtained are shown in Table 1 below.

Example 3

A liquefied product was obtained in the same manner as in Example 1, except that the pressure at the time of heating in the conduction heating type drying device was set to 0.12 MPa and the surface temperature of the hollow disc (disc) was changed to 105° C.

The recovery rates of ethanol, 2,3-BDO, acetic acid, and water were determined in the same manner as in Example 1 and were 95 volume %, 65 volume %, 67 volume %, and 100 volume %, respectively. The results obtained are shown in Table 1 below.

Example 4

A liquefied product was obtained in the same manner as in Example 1, except that the pressure at the time of heating in the conduction heating type drying device was set to 0.08 MPa and the surface temperature of the hollow disc (disc) was changed to 95° C.

The recovery rates of ethanol, 2,3-BDO, acetic acid, and water were measured in the same manner as in Example 1 and were found to be 72 volume %, 55 volume %, 51 volume %, and 95 volume %, respectively. The results obtained are shown in Table 1 below.

Example 5

A liquefied product was obtained in the same manner as in Example 1, except that the pressure at the time of heating in the conduction heating type drying device was set to 0.05 MPa and the surface temperature of the hollow disc (disc) was changed to 85° C.

The recovery rates of ethanol, 2,3-BDO, acetic acid, and water were determined in the same manner as in Example 1 and were 65 volume %, 50 volume %, 41 volume %, and 82 volume %, respectively. The results obtained are shown in Table 1 below.

TABLE 1

| | Surface temperature - boiling point of ethanol (° C.) | Recovery Rate (% by vol.) | | | |
|---|---|---|---|---|---|
| Surface temperature (° C.) | | ethanol | 2,3-BDO | Acetic acid | water |
| Ex. 1 | 100 | 22 | 93 | 56 | 58 | 100 |
| Ex. 2 | 115 | 37 | 95 | 78 | 74 | 100 |
| Ex. 3 | 105 | 27 | 95 | 65 | 67 | 100 |
| Ex. 4 | 95 | 17 | 72 | 55 | 51 | 95 |
| Ex. 5 | 85 | 7 | 65 | 50 | 41 | 82 |

Comparative Example 1

A foaming test by bubbling was also conducted on the organic substance-containing liquid used in Example 1, and vigorous foaming was confirmed.

From the above results, it has become clear that the liquefied product obtained by heating an organic substance-containing liquid comprising microorganisms, separating the liquid or solid component comprising microorganisms and the gaseous component containing the organic substance, and condensing the gaseous component can suppress foaming in the subsequent purification process.

The invention claimed is:

1. A method for producing an organic substance, comprising:
    a microbial fermentation step of obtaining an organic substance-containing liquid by microbial fermentation, and
    a separation step of heating the organic substance-containing liquid which is a suspension by using a conduction heating type dryer and separating into a liquid or solid component comprising microorganisms and a gaseous component comprising the organic substance.

2. A method for producing an organic substance, comprising:
    a microbial fermentation step of obtaining an organic substance-containing liquid comprising an organic substance having a boiling point of 115° C. or lower and an organic substance having a boiling point of over 115° C. by microbial fermentation, and
    a separation step of heating the organic substance-containing liquid which is a suspension by using a conduction heating type dryer and separating into a liquid or solid component comprising the organic substance having a boiling point of over 115° C. and microorganisms, and a gaseous component comprising the organic substance having a boiling point of 115° C. or lower, wherein
    the heating temperature is from the boiling point of the organic substance having a boiling point of 115° C. or lower to 130° C.

3. The method according to claim 1, further comprising a liquefaction step of liquefying the gaseous component obtained by the separation step by condensation, wherein condensation heat generated in the liquefaction step is used as a heat source.

4. The method according to claim 3, further comprising a purification step of purifying the organic substance by heat distillation, wherein
  the condensation heat is used for a heat source of the heat distillation of the purification step.

5. The method according to claim 1, wherein
  the microbial fermentation uses a syngas comprising carbon monoxide as a raw material.

6. The method according to claim 5, wherein
  the syngas is a waste-derived gas.

7. The method according to claim 1, wherein the organic substance comprises alcohol having 1 to 6 carbons.

8. The method according to claim 2, further comprising a liquefaction step of liquefying the gaseous component obtained by the separation step by condensation, wherein
  condensation heat generated in the liquefaction step is used as a heat source.

9. The method according to claim 8, further comprising a purification step of purifying the organic substance by heat distillation, wherein
  the condensation heat is used for a heat source of the heat distillation of the purification step.

10. The method according to claim 2, wherein
  the microbial fermentation uses a syngas comprising carbon monoxide as a raw material.

11. The method according to claim 10, wherein
  the syngas is a waste-derived gas.

12. The method according to claim 2, wherein
  the organic substance comprises alcohol having 1 to 6 carbons.

* * * * *